US00PP21569P2

(12) United States Plant Patent
Rockwood

(10) Patent No.: US PP21,569 P2
(45) Date of Patent: Dec. 14, 2010

(54) ***EUCALYPTUS* TREE NAMED 'G3'**

(50) Latin Name: *Eucalyptus grandis*
Varietal Denomination: G3

(75) Inventor: Donald L. Rockwood, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/587,764

(22) Filed: Oct. 13, 2009

(51) Int. Cl.
*A01H 5/00* (2006.01)

(52) U.S. Cl. ..... Plt./216

(58) Field of Classification Search ..... Plt./216
See application file for complete search history.

*Primary Examiner*—Annette H Para
(74) *Attorney, Agent, or Firm*—Jondle & Associates, P.C.

(57) ABSTRACT

A new *Eucalyptus grandis* tree particularly distinguished by having a fast growth rate, good frost tolerance, and good coppicing properties, is disclosed.

4 Drawing Sheets

ACKNOWLEDGEMENT OF FEDERAL RESEARCH SUPPORT

The present invention was supported in part by funds from the U.S. Government. The U.S. Government therefore may have certain rights in the invention.

Genus and species: *Eucalyptus grandis.*

Variety denomination: 'G3'.

BACKGROUND OF THE NEW PLANT

The present invention comprises a new and distinct variety of *Eucalyptus*, botanically known as *Eucalyptus grandis*, and hereinafter referred to by the variety name 'G3'. It is characterized by having a fast growth rate, good frost tolerance, and good coppicing properties when grown under normal forestry practices in central and southern Florida.

'G3' originated from a group of 31,725 seedlings of *Eucalyptus grandis*. 'G3' is the result of open-pollination in a third-generation seedling seed orchard at Palmdale, Fla. The female (seed) parent of 'G3' is the proprietary *Eucalyptus grandis* seedling selection with the identification number '1136' (unpatented) characterized by its fast growth and average frost tolerance. The male (pollen) parent of 'G3' is unknown. The maternal parent (1136) originated from open-pollination. The female (seed) parent of '1136' is the proprietary *Eucalyptus grandis* seedling selection with the identification number '290' (unpatented) characterized by its good growth and acceptable frost tolerance. The male (pollen) parent of '1136' is unknown. 'G3' was selected as a single clone from the progeny of the above stated open-pollination during February 1982.

'G3' was first asexually propagated in June of 2007 in Lake Alfred, Fla. through cuttings and in vitro propagation. Asexually propagated trees of 'G3' have remained true to the original selected tree, and all characteristics of the tree have been transmitted and retained through three successive asexual vegetative generations.

Plant Breeder's Rights for this cultivar have not been applied for. 'G3' has not been made publicly available more than one year prior to the filing of this application.

DESCRIPTION OF THE PHOTOGRAPHS

This new *eucalyptus* tree is illustrated by the accompanying photographs which show the tree's form and foliage. The colors shown are as true as can be reasonably obtained by conventional photographic procedures. The photographs are of a tree approximately 13 years old.

Figure 1:
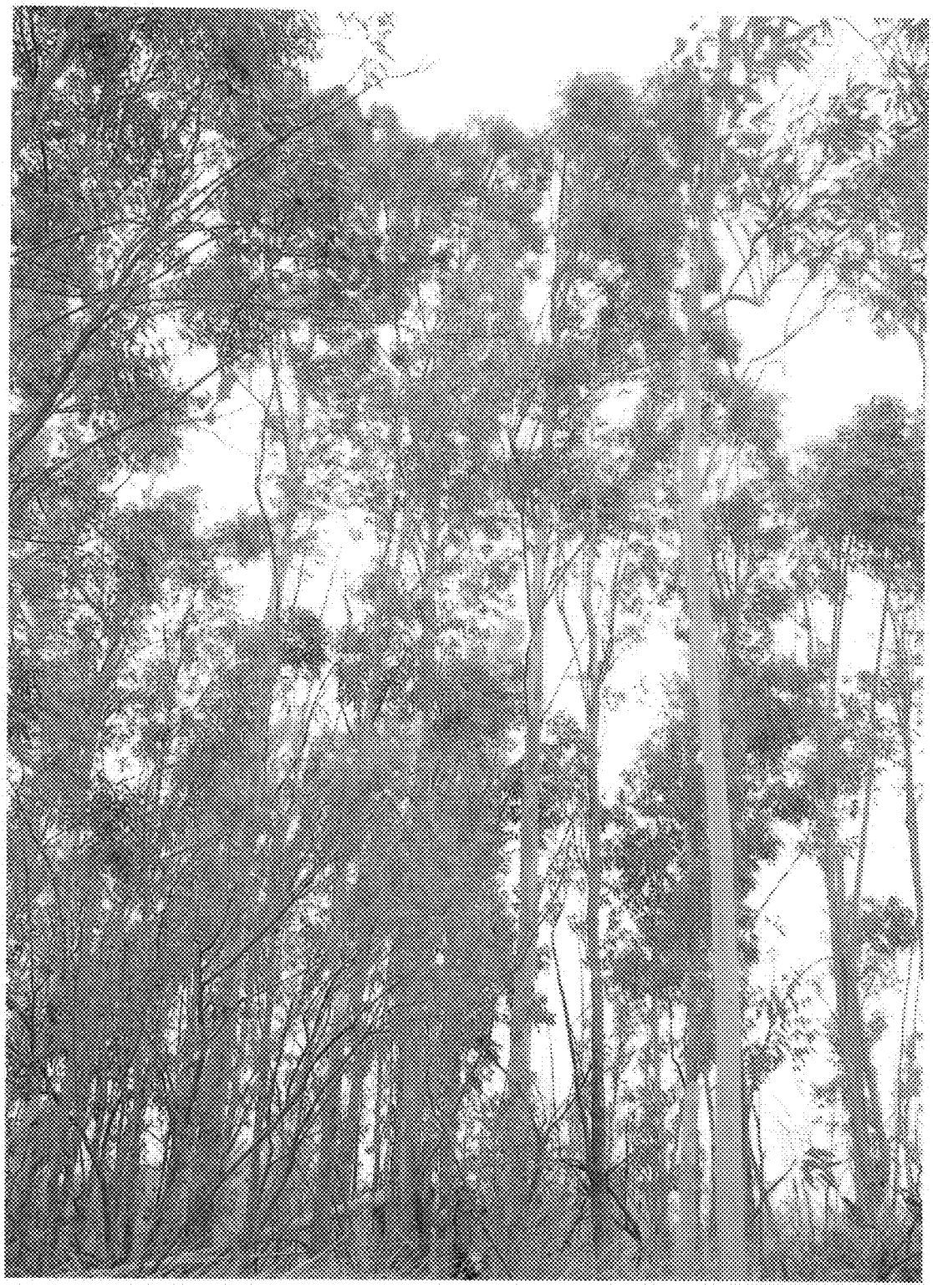
Figure 2:
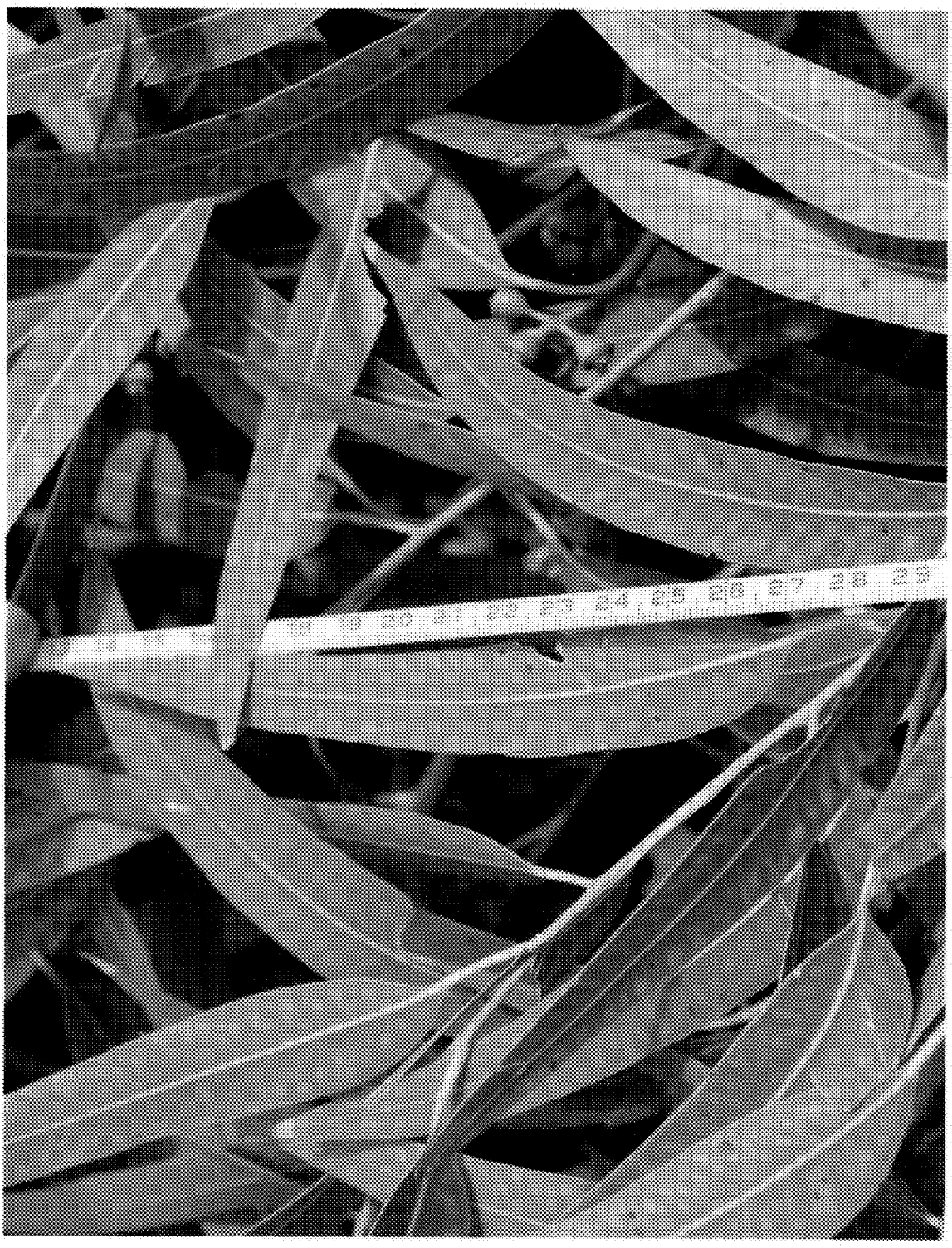
Figure 3:
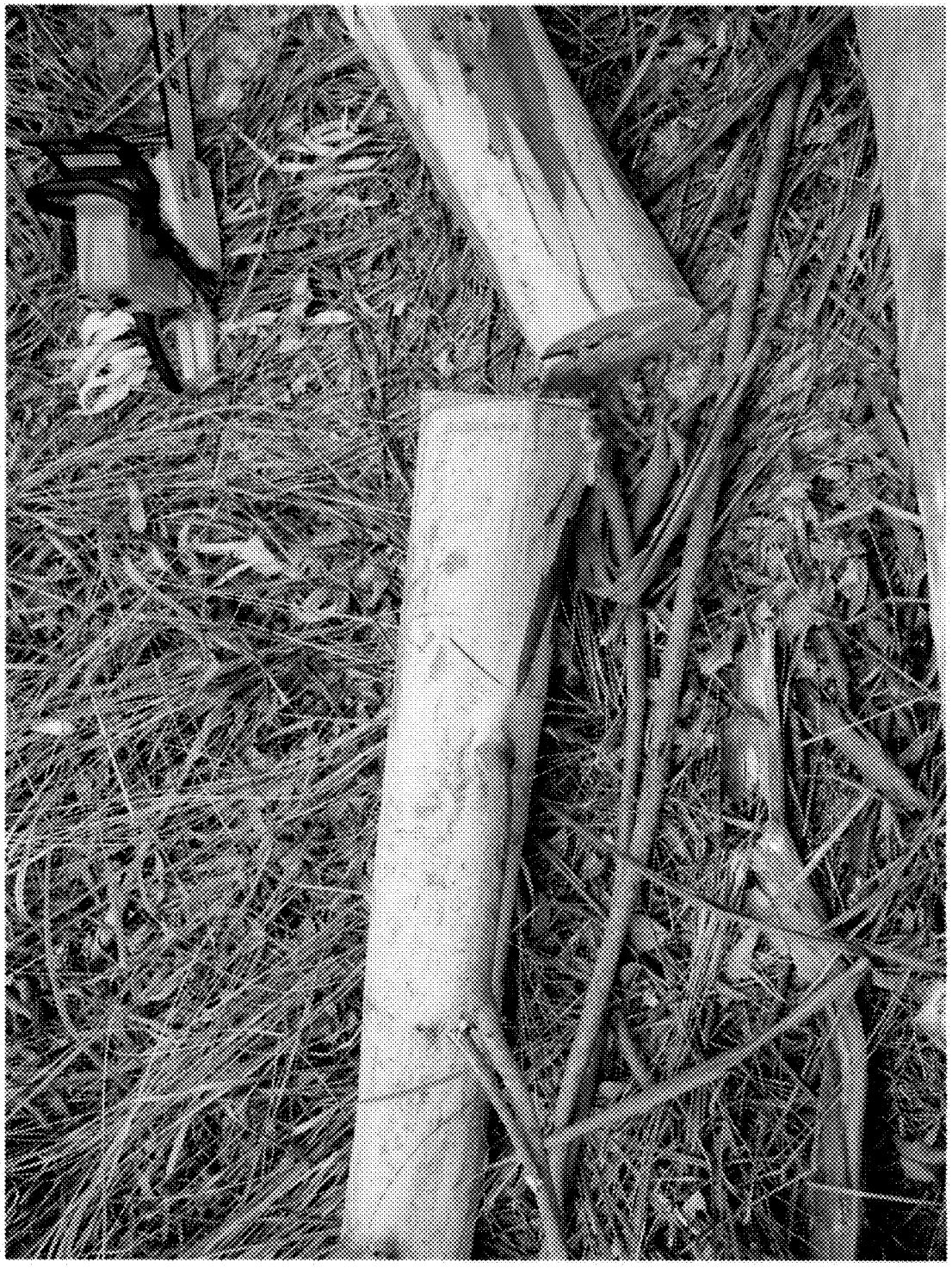
Figure 4:
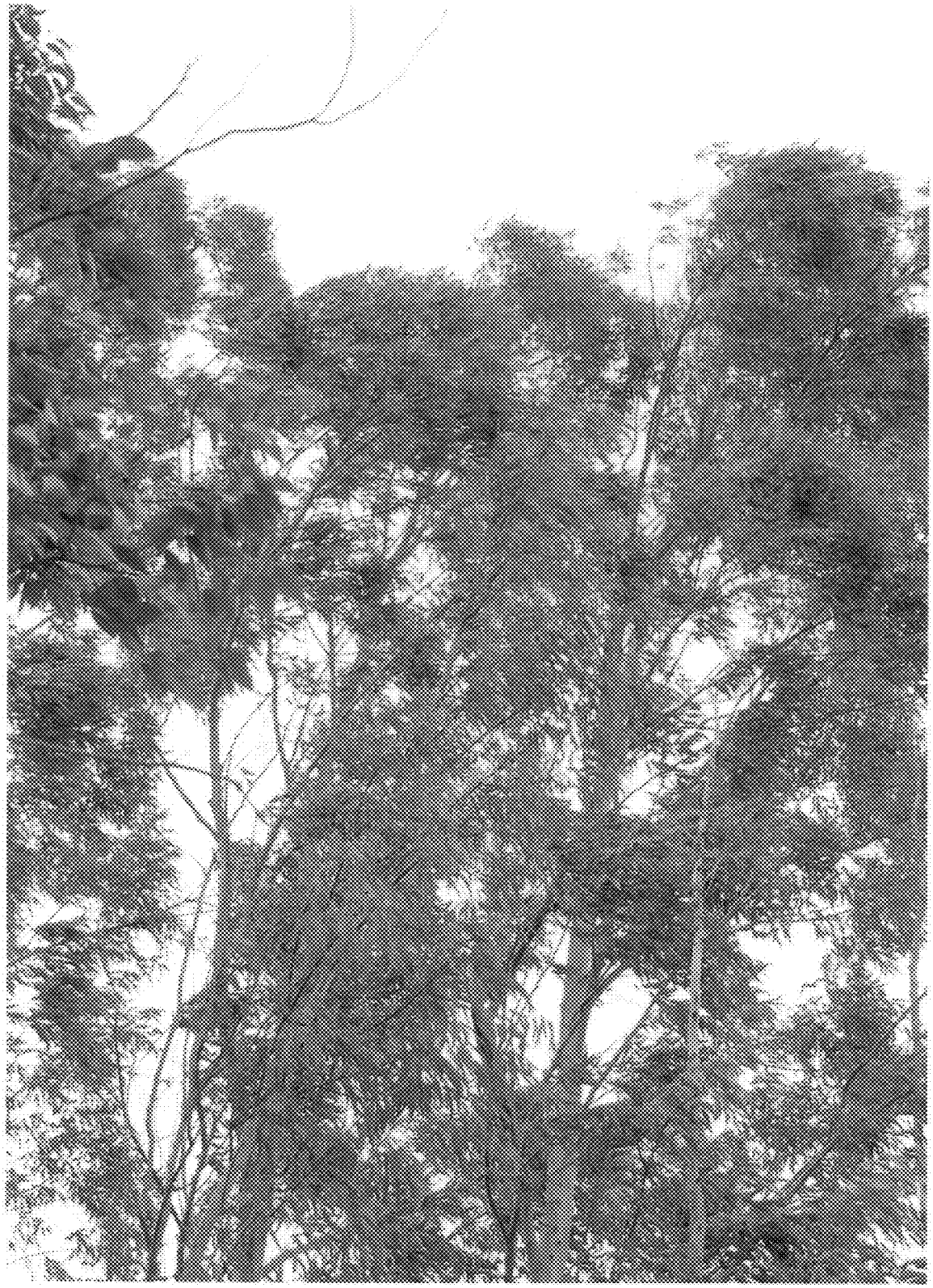

FIG. 1 shows the overall plant habit including foliage.
FIG. 2 shows a close-up of the mature leaves.
FIG. 3 shows a close-up of the trunk.
FIG. 4 shows the branches and crown of the tree.

DESCRIPTION OF THE NEW CULTIVAR

The following detailed description sets forth the distinctive characteristics of 'G3'. The present botanical description is that of 13-year-old trees growing at the University of Florida's research site near Mulberry, Fla. The colors (except those in common terms) are described from R.H.S. Colour Chart published by The Royal Horticultural Society in London (second edition), in association with the Flower Council of Holland.

DETAILED BOTANICAL DESCRIPTION

Classification:
- *Botanical.*—*Eucalyptus grandis* var. 'G3'.
- *Common name.*—*Eucalyptus.*

Parentage:
- *Female parent.*—'1136' (unpatented).
- *Male parent.*—Unknown.

Tree:
- *Size.*—Height: About 16.0 m. Spread: About 3.0 m.
- *Vigor.*—Good.
- *Density.*—Open.
- *Form (overall shape of tree).*—Narrowly upright with somewhat drooping branches.
- *Growth habit.*—Evergreen.

Trunk and branches:
- *Trunk texture.*—Smoother at top.
- *Trunk bark color.*—Mottled grey, brown, green.
- *Branch texture.*—Glabrous.

*Branch color.*—Green with some reddish-brown mottling.

Leaves:

*Size* (*lamina average*).—Length: 10.0 cm to 16.0 cm. Width: 1.5 cm to 2.5 cm.

*Type.*—Simple, petiolate, alternate, persistent.

*Shape.*—Narrow lanceolate, slightly sickle shaped.

*Apex.*—Acuminate.

*Base.*—Acute, can be slightly unequilateral.

*Margin.*—Smooth, wavy.

*Surface texture* (*both surfaces*).—Glabrous.

*Color.*—Upper surface: RHS 136B (Green). Lower surface: RHS 136C (Green).

*Petiole.*—Shape: Slightly flattened with a groove at top. Length: 1.5 cm to 2.5 cm. Width: 0.1 cm to 0.2 cm. Color: RHS 144D (Pale green-pink). Texture: Smooth.

Flowers:

*Type.*—Clustered.

*Blossom period.*—Mid-August to late-October.

*Fragrance.*—Mild.

Reproductive organs:

*Stamen number.*—Many.

*Anther color.*—White.

*Anther filament length.*—About 1.0 cm.

*Pistil number.*—1.

*Pistil length.*—About 1.0 cm.

Fruit/seed (if produced):

*Size.*—Length: 0.5 cm to 0.7 cm. Width: 0.5 cm to 0.6 cm.

*Shape.*—Pyriform.

*Texture.*—Smooth woody.

*Apex.*—Star-shaped.

*Base.*—Attenuate.

*Color.*—Immature: Green. Mature: Brown.

*Stalk.*—Short.

Resistance/tolerance to diseases/pests: No unusual susceptibilities noted.

COMPARISON WITH PARENTAL AND KNOWN VARIETIES

'G3' differs from the female parent '1136' (unpatented) by having faster growth and better frost tolerance than '1136'. In addition, 'G3' had good coppicing properties.

There are no commercial varieties known to the inventor which can be compared with 'G3'.

I claim:

1. A new and distinct variety of *Eucalyptus grandis* tree as shown and described herein.

* * * * *